United States Patent [19]

Tujisawa et al.

[11] Patent Number: 4,732,591

[45] Date of Patent: Mar. 22, 1988

[54] AIR-CLEANING APPARATUS

[75] Inventors: Yoshimoto Tujisawa; Hideo Fukai, both of Kyoto, Japan

[73] Assignee: Daido-Maruta Finishing Co., Ltd., Kyoto, Japan

[21] Appl. No.: 11,813

[22] Filed: Feb. 6, 1987

[30] Foreign Application Priority Data

Jul. 15, 1986 [JP] Japan .................. 61-108883

[51] Int. Cl.$^4$ ............................................. B01D 46/10
[52] U.S. Cl. ........................................ 55/279; 55/316; 55/385 A; 55/385 G; 131/231; 131/329; 422/123; 422/124
[58] Field of Search ............... 55/279, 316, 385 A, 55/385 G, 472; D23/149, 150; 131/231, 238, 329, 330; 422/123, 124, 316

[56] References Cited

U.S. PATENT DOCUMENTS

| | | | |
|---|---|---|---|
| 1,239,515 | 9/1917 | Peterson ........................ | D23/158 |
| 4,154,251 | 5/1979 | Doyel ............................. | 131/231 |
| 4,231,379 | 11/1980 | Kohori ........................... | 55/385 G X |
| 4,244,710 | 1/1981 | Burglr ............................ | 55/279 X |
| 4,377,399 | 3/1983 | Bryson ........................... | 422/124 X |

Primary Examiner—Charles Hart
Attorney, Agent, or Firm—Armstrong, Nikaido, Marmelstein & Kubovcik

[57] ABSTRACT

An air-cleaning apparatus presenting an appearance of a flowerpot comprises: a hollow container provided with a ventilating hole in its lower portion and an opening in its upper portion; a fan disposed inside the container; driving means for driving the fan; an air-cleaning filter disposed above the ventilating hole; an air-permeable supporting plate disposed above the fan and the filter; and a natural and/or imitation garden plant mounted on the supporting plate, which plant is covered at its root with an air-permeable filter.

11 Claims, 2 Drawing Figures

FIG. 1
FIG. 2
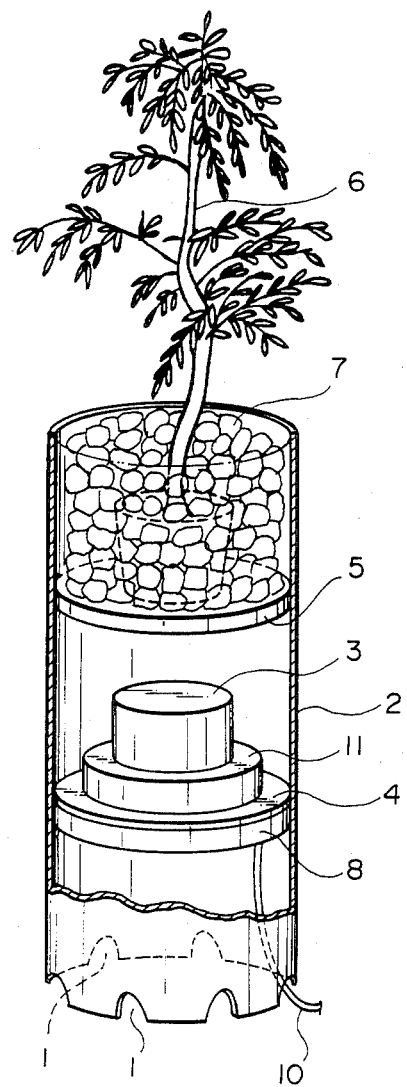
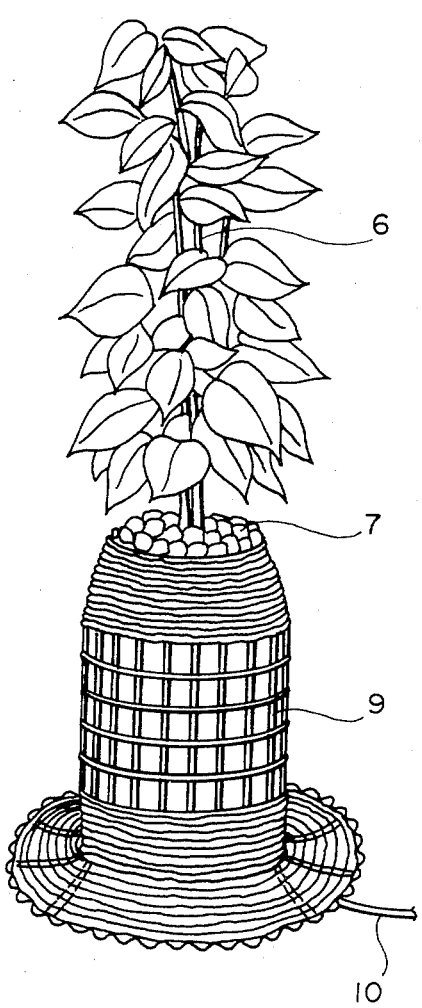

AIR-CLEANING APPARATUS

BACKGROUND OF THE INVENTION

1. Field of the Invention

The present invention relates to an air-cleaning apparatus presenting an ornamental appearance.

2. Description of the Prior Art

An air-cleaning apparatus, in which a fan draws air from the atmosphere in a room and after filtering out impurities of the air for cleaning the same, the thus obtained clean air is returned to the room, is publicly known. However, in appearance, any of such conventional air-cleaning apparatus is merely boxy and mechanical, and thereby lacks ornamentality. As a result, the conventional air-cleaning apparatus is rarely employed except when the use thereof is inevitable, though it is employed in some of the meeting room of a firm and the exhibition room of an art museum.

SUMMARY OF THE INVENTION

It is an object of the present invention to provide an air-cleaning apparatus which presents an ornamental appearance to make it possible that the air-cleaning apparatus of the present invention is employed in harmony with any place.

The air-cleaning apparatus of the present invention presents an appearance of a flowerpot and is characterized in construction by comprising: a hollow container provided with a ventilating hole in its lower portion and an opening in its upper portion; a fan provided inside the container at a position above the ventilating hole, for drawing air from the atmosphere and driving the air upward; a driving means for driving the fan; air-cleaning filter means disposed above the ventilating hole at a position above and/or under the fan; an air-permeable supporting plate disposed above the fan and the filter means; and a natural and/or imitation garden plant including a flowering plant, disposed on the supporting plate, which garden plant is covered at its root with an air-permeable filler.

BRIEF DESCRIPTION OF THE DRAWINGS

FIG. 1 is a perspective view of an embodiment of the air-cleaning apparatus of the present invention; and FIG. 2 is a perspective view of another embodiment of the apparatus of the present invention.

DESCRIPTION OF THE PREFERRED EMBODIMENTS

In the air-cleanihg apparatus of the present invention, filter means and a fan are provided inside a hollow container provided with a ventilating hole which is located in a lower portion of the container, so that the fan draws air from the atmosphere through the ventilating hole into the container and after cleaning the air by the use of the filter means, the thus obtained clean air is released from the container through its upper opening portion. At this time, since a garden plant is disposed on an air-permeable supporting plate which is provided in an upper portion of the container at a position above the fan while covered at its root with an air-permeable filler in a stable manner to present an appearance of a natural garden plant received in a normal flowerpot, the leaves of such garden plant slightly wave under the influence of the clean air released upward from the upper opening portion of the container by means of the fan.

In the apparatus of the present invention, the fan and its driving means may be the sames as those employed in a conventional air-cleaning apparatus or a conventional exhaust fan. In addition, a power-supply cord of the driving means such as an electric motor and the like may extend outward through the ventilating hole of the container or may be directly mounted on a side surface of the container.

The fan may be supported at a predetermined position by means of the supporting plate which is mounted on an inner surface of the container. However, preferably, the fan is mounted on a supporting plate which is an air-permeable one provided inside the container.

The filter means may be made of nonwoven fabrics, filter papers and the like, and preferably contains at least one of air-cleaning additives such as activated charcoal, deodorant agents, dust-attracting agents, hygroscopic agents, anti-fungus agents, sterilizing agents and the like. These additives are mainly employed in the form of powders or pellets. However, it is also possible that these additives are impregnated into or applied to the filter means in the form of liquid.

The filter means is so disposed inside the container that the interior of the container is completely partitioned into cubicles at a position above or under the fan to make it possible that all the air driven by the fan passes through the filter means. In this connection, the filter means is preferably disposed along the supporting plate such as one for supporting the fan thereon or one for supporting the garden plant thereon, in order to make its handling easy to lead to the convenience of the apparatus of the present invention in use.

In order to facilitate the replacement of the filter means, it is also possible to partition the container at a position between the filter means and the supporting plate for supporting the garden plant thereon. Also may be provided inside the container are a moisturizing means for moisturizing the air and an odoriferous substance for improving the perfume of the air.

The moisturizing of the air may be realized by placing a petri dish containing water and/or cloth or cotton impregnated with water on a bottom portion of the container or on the supporting plate for supporting the garden plant or fan thereon, or also realized by moisturizing the filter means or the filler for covering the root of the garden plant. Incidentally, the odoriferous substance may also be provided inside the container in the same manner as that described above.

More particularly, it is preferable to employ small pieces of porous unglazed-potteries as the filler for covering the root of the garden plant according to the present invention. For example, such small pieces of unglazed-potteries may be commercially available ones which are substitutes for the horticultural soil.

In use, the small pieces of unglazed-potteries graded 8 to 15 mm in particle-diameter are employed as the filler. In this case, preferably, the deodorant agent is absorbed by at least a part of such filler to be employed. In general, the deodorant agent is strongly absorbed to the inside of such filler to provide the filler with a deodorant effect for an extended period of time, so that such filler realizes a very effective air-cleaning performance.

Any of the commercially available deodorant products may be employed as the deodorant agent in the present invention. In case that the deodorant agent is one containing a liquid deodorant-component obtained from mainly leaves of the theaceous plants, it is found that the deodorant effect of such one lasts at least 1 year.

Incidentally, according to the present invention, the container may directly present an ornamental appearance. In addition, it is also possible that the container is made of a transparent plastic and received in an ornamental outer-casing such as a ceramic flowerpot, a basket made from rattan or bamboo and the like.

Now, an embodiment of the air-cleaning apparatus of the present invention will be hereinbelow described with reference to the drawings.

As shown in FIG. 1, a hollow container 2 of the embodiment of the air-cleaning apparatus of the present invention is provided with a ventilating hole 1 at its lower end portion and an opening at its upper end portion. Inside the container 2 are mounted a pair of air-permeable upper 5 and lower 8 supporting plates. A filter 4 made of nonwoven fabrics containing activated charcoal is disposed on the lower supporting plate 8, on which filter 4 is mounted a motor 11 having a fan 3. The motor 11 acts as a driving means for driving the fan 3 to drive air upward. Disposed on the upper supporting plate 5 is a garden plant 6 which is constructed of a natural tree and imitation leaves fitted thereto. The thus constructed garden plant 6 is covered at its root with a filler 7 such as porous synthetic-resin pieces or a dry sphagnun, to allow the air driven upward to pass therethrough while presenting an appearance of a natural tree planted in soil. Incidentally, preferably, at least one of the upper 5 and lower 8 supporting plates is constructed of a reticulated metallic plate or reticulated plastic plate.

In the air-cleaning apparatus of the present invention provided with the above construction, a cord 10 is connected to a power-supply to provide the motor 11 with a power. The fan 3 is driven by the motor 11 to draw air from the atmosphere in a room into the container 2 and after cleaning the air, the thus cleaned air is released outward from the upper end opening of the container 2 to the room to clean the atmosphere in the room. At this time, the garden plant planted in the upper end portion of the air-cleaning apparatus of the present invention is slightly waved at its leaves by the clean air released from its root, to present a natural and very comfortable appearance thereof.

In the apparatus of the present invention, as the container 2, an ornamental one may be directly employed. However, as shown in FIG. 2, it is also possible to employ an ornamental outer casing 9 for covering the plain container 2. In the latter case, it is possible to provide a large ornamental effect by employing a rattan basket or a ceramic flowerpot as such outer casing 9.

Incidentally, in the above embodiment of the present invention, as an example of the filler 7, small pieces of a brick-red unglazed potteries graded 8 to 15 mm in particle-diameter impregnated with a deodorant product "Fresh Shiraimatsu" was employed and showed an effective air-cleaning performance excellent in deodorant effect, which "Fresh Shiraimatsu" is described in U.S. Pat. No. 4,501,730 issued Feb. 26, 1985 and is commercially available from Shiraimatsu Sinyaku Kabushiki Kaisha. In this case, tobacco's smell and smoke did not become a substantial problem even in a room accommodating many smokers. In addition, in this case, by employing an electrostatic air-filter as the filter 4, it is possible to eliminate tobacco's smoke and nicotine, while by the use of the filler 7 it is possible to eliminate the tobacco's smell, to lead to a better results in air-cleaning.

The small pieces of the unglazed potteries described above are impregnated with a treatment-liquid containing 2 to 3% of a deodorant agent, and dried to prepare a ceramic filler having a deodorant effect which is identified, for example, as follows: namely, 50 g of the thus prepared ceramic filler is received in a 1-liter vessel to which is then added 1 ml of 4%-ammonia and after keeping stationary for 20 minutes, the residual gas is measured to identify an elimination rate of at least 80% of ammonia smell.

The following tests are conducted by the use of 1 $m^3$-sealed vessel in which a predetermined amount of the above ceramic filler as the filler 7 having been received, for clarifying the deodorant effect of the ceramic filler:

A: trimethylamine-test 3 ml of 30%-trimethylamine is received in the vessel, and then the vessel is sealed to be kept stationary for 1 hour. After that, headspace gas of the thus sealed vessel is sampled, and analyzed by gas chromatography to determine a peak area which is compared with that determined in a similar test conducted without employing the ceramic filler, so that an elimination rate of the trimethylamine is determined.

B: ammonia-test 5 ml of 28%-ammonia is received in the vessel, and then the vessel is sealed to be kept stationary for 1 hour. After that, headspace gas of the sealed vessel is sampled, and subjected to a color identification through an indophenol-method so as to determine a color reaction thereof by means of a spectrophotometer in a manner of absorbance-measurement in 630 nm. The thus determined result of the color reaction is then compared with that obtained in a similar test conducted without employing the deodorant ceramic filler, so that an elimination rate of the ammonia is determined.

C: hydrogen sulfide-test

Hydrogen sulfide gas is received in the vessel, and then the vessel is sealed to be kept stationary for 1 hour. After that, headspace gas of the sealed vessel is sampled, and subjected to a color identification through a methylene blue-method so as to determine a color reaction thereof by means of the spectrophotometer in a manner of the absorbance-measurement in 66 nm. The thus determined result of the color reaction is then compared with that determined in a similar test conducted without employing the deodorant ceramic filler, so that an elimination rate of the hydrogen sulfide is determined.

D: acetic acid-test 10 ml of acetic acid is received in the vessel, and then the vessel is sealed to be kept stationary for 1 hour. After that, headspace gas of the sealed vessel is sampled, and analyzed by gas chromatography to determine a peak area which is compared with that determined in a similar test conducted without employing the deodorant ceramic filler, so that an elimination rate of the acetic acid is determined.

E: smoke-test

An alcohol having absorbed a white smoke is received in the vessel while subjected to a bubbling action therein for 1 hour. After that, headspace gas of the vessel is sampled and analyzed by the gas chromatography to determine a peak area which is compared with that determined in a similar test conducted without employing the deodorant ceramic filler, so that an elimination rate of the smoke is determined.

The results of the above tests are shown in the following Table 1:

TABLE 1

| Kind of Test | Amount of Ceramic filler (g) | Elimination Rate (%) |
| --- | --- | --- |
| A. trimethylamine | 200 | 95.3 |
| B. ammonia | 200 | 83.8 |
| C. hydrogen sulfide | 200 | 98.0 |
| D. acetic acid | 200 | 68.1 |
| E. smoke | 100 | 28.0 |

In addition, the deodorant effect of the trimethylamine is calculated on the basis of a restriction level of smell in Tokyo, which level is 0.005 ppm/day, so that an effective service life of the deodorant ceramic filler is clarified as follows:

| Room Size (Jyo) | Amount of Ceramic filler (g) | Usable Life (month) |
| --- | --- | --- |
| 20 | 50 | 2 |
|  | 100 | 4 |
|  | 200 | 8 |
|  | 300 | 14 |
| 6 | 50 | 6 |
|  | 100 | 14 |
|  | 200 | 29 |
|  | 300 | 43 | wherein: the "Jyo" is one of Japanese traditional units of area, which corresponds to approximately 3.3/2 m².

Since the air-cleaning apparatus of the present invention has a sufficient air-cleaning performance and presents an appearance of a flowerpot, the apparatus is excellent in ornamentality to itself harmonious with any kind of room. In addition, the leaves of the garden plant planted in the apparatus are slightly waved by the clean air released from the root of such garden plant upward, to make the plant vivid in its appearance.

Further, in the air-cleaning apparatus of the present invention, as the filler, such ceramic filler having been impregnated with an deodorant agent is employed to enable the apparatus to have a more advanced air-cleaning performance.

What is claimed is:

1. An air-cleaning apparatus presenting an appearance of a flowerpot, comprising: a hollow container provided with a ventilating hole in its lower portion and an opening in its upper portion; a fan provided inside said container at a position above said ventilating hole, for drawing air from the atmosphere and driving said air upward; a driving means for driving said fan; air-cleaning filter means disposed above said ventilating hole at a position above and/or under said fan; an air-permeable supporting plate disposed above said fan and said filter means; and a natural and/or imitation garden plant including a flowering plant, disposed on said supporting plate, said garden plant being covered at its root with an air-permeable filler.

2. The air-cleaning apparatus as set forth in claim 1, wherein: said container can be partitioned into cubicles at a position between said filter means and said supporting plate.

3. The air-cleaning apparatus as set forth in claim 1 or 2, wherein: said fan is disposed on said air-permeable supporting plate.

4. The air-cleaning apparatus as set forth in claim 3, wherein: said supporting plate is made of a reticulated metallic plate or a reticulated plastic plate.

5. The air-cleaning apparatus as set forth in claim 3, wherein: at least one of activated charcoal, deodorant agents, dust-attracting agents, hygroscopic agents, anti-fungus agents and sterilizing agents is contained in said filter means.

6. The air-cleaning apparatus as set forth in claim 3, wherein: a moisturizing means is provided inside said container.

7. The air-cleaning apparatus as set forth in claim 3, wherein: an odoriferous substance is provided inside said container.

8. The air-cleaning apparatus as set forth in claim 3, wherein: said container is housed in an ornamental outer casing.

9. The air-cleaning apparatus as set forth in claim 3, wherein: porous small pieces of unglazed-potteries are employed as said filler.

10. The air-cleaning apparatus as set forth in claim 3, wherein: at least a part of said small pieces of said unglazed-potteries is impregnated with a deodorant agent.

11. The air-cleaning apparatus as set forth in claim 10, wherein: said deodorant agent comprises a liquid deodorant-component obtained from mainly leaves of theaceous plants.

* * * * *